United States Patent
Padula et al.

(10) Patent No.: US 11,747,617 B2
(45) Date of Patent: Sep. 5, 2023

(54) SYSTEMS AND METHODS FOR A PARALLACTIC AMBIENT VISUAL-FIELD ENHANCER

(71) Applicant: Veyezer, LLC, Killingworth, CT (US)

(72) Inventors: William V. Padula, Killingworth, CT (US); Craig Eugene Andrews, Loudon, TN (US)

(73) Assignee: Padula Rehabilitation Technologies, LLC, Guilford, CT (US)

( * ) Notice: Subject to any disclaimer, the term of this patent is extended or adjusted under 35 U.S.C. 154(b) by 300 days.

(21) Appl. No.: 16/938,201

(22) Filed: Jul. 24, 2020

(65) Prior Publication Data
US 2022/0026711 A1 Jan. 27, 2022

(51) Int. Cl.
*G02B 27/01* (2006.01)
*G06F 3/01* (2006.01)

(52) U.S. Cl.
CPC ........ *G02B 27/0101* (2013.01); *G06F 3/013* (2013.01); *G02B 2027/0123* (2013.01); *G02B 2027/0129* (2013.01)

(58) Field of Classification Search
None
See application file for complete search history.

(56) References Cited

U.S. PATENT DOCUMENTS

| | | | |
|---|---|---|---|
| 8,262,590 B2 | 9/2012 | Padula | |
| 8,567,950 B2 | 10/2013 | Padula | |
| 10,856,796 B1* | 12/2020 | Berme | G06F 3/013 |
| 10,888,771 B2* | 1/2021 | Joshi | G06F 3/04892 |
| 11,210,816 B1* | 12/2021 | An | G06T 11/00 |
| 11,250,617 B1* | 2/2022 | Sempe | H04L 65/611 |
| 2010/0171926 A1* | 7/2010 | Padula | A61B 3/024 351/224 |
| 2010/0253676 A1* | 10/2010 | Mumbauer | G06T 15/20 345/419 |
| 2017/0000326 A1 | 1/2017 | Samec et al. | |
| 2017/0124762 A1* | 5/2017 | Privault | G06F 3/011 |
| 2017/0249021 A1* | 8/2017 | Henrique Barbosa Postal | G06F 3/011 |
| 2017/0329488 A1* | 11/2017 | Welker | G06T 19/006 |
| 2018/0136816 A1* | 5/2018 | Tao | G06F 3/012 |
| 2018/0197324 A1* | 7/2018 | Hanamoto | G06T 15/205 |

(Continued)

FOREIGN PATENT DOCUMENTS

CN 107592798 A 1/2018

OTHER PUBLICATIONS

PCT/US2021/42755, Jul. 22, 2021, N/A.

*Primary Examiner* — Fred Tzeng
(74) *Attorney, Agent, or Firm* — McCarter & English, LLP

(57) ABSTRACT

A method for creating a temporal-spatial dissociation between an ambient visual process and a focal visual process of a user is provided. The method includes rendering, via a parallactic ambient visual-field enhancing (PAVE) module configured to execute on a computing device communicatively coupled to a head mounted display device worn by a user, a fixation target and a background located behind the fixation target displayed within the head mounted display device. The method further includes updating, via the PAVE module, the rendering of the background within the head mounted display device, wherein the update comprises a virtual movement of the background behind the fixation target.

20 Claims, 6 Drawing Sheets

(56) References Cited

U.S. PATENT DOCUMENTS

| | | | |
|---|---|---|---|
| 2018/0307397 A1* | 10/2018 | Hastings | G06F 3/017 |
| 2019/0261847 A1* | 8/2019 | Padula | A61B 3/103 |
| 2020/0113434 A1* | 4/2020 | Padula | G02B 27/0172 |
| 2020/0126304 A1* | 4/2020 | Jelmi | G02B 27/017 |
| 2021/0275013 A1* | 9/2021 | Alvarez | G02B 27/017 |

* cited by examiner

SYSTEMS AND METHODS FOR A PARALLACTIC AMBIENT VISUAL-FIELD ENHANCER

BACKGROUND

1. Technical Field

Systems, methods, apparatus, and non-transitory computer readable medium are described for a holographic and/or virtual based parallactic ambient visual-field enhancer to create a temporal-spatial dissociation between an ambient visual process and a focal visual process of a user.

2. Background Art

Persons incurring neurologic events such as a traumatic brain injury (TBI) or cerebrovascular accident (CVA) can result in visual field loss and/or spatial neglect. For the purpose of this disclosure, the term visual field loss or field loss will also include spatial neglect. The field loss or neglect will often be projected to the same field of view for each eye. This means that a neurological event affecting the right cerebral cortex will cause a field loss in the left field of both eyes. This is termed a left homonymous hemianopsia. A lesion affecting the left cerebral cortex will produce a field loss for each eye on the right side. This is termed a right homonymous hemianopsia.

This type of vision impairment will cause significant interference in function and performance. Homonymous hemianopsias will directly affect spatial orientation, posture, and balance. Persons with this resultant condition will frequently bump into objects on one side and are more susceptible to injury from trauma or falls. This is due to the homonymous hemianopsia causing a Visual Midline Shift Syndrome (VMSS) which affects the concept of the ego center or visual midline in addition to the blind spot produced by the field loss. In addition, reading becomes difficult. A right homonymous hemianopsia interferes because the spatial visual field loss blocks the next word to be read. Consequently, a left homonymous hemianopsia causes difficulty shifting gaze from the end of the line of print on the right side to the beginning of the next line of print.

In addition, homonymous hemianopsia interferes with daily living skills. Activities such as shopping in a store, conversing in a group of people, and even finding food on the plate will become very challenging. In turn, homonymous hemianopsia will affect socialization and reduce independence. A person with a homonymous hemianopsia is most often not safe to drive. This will in turn affect employment, earning potential, family relationships, to name several.

Persons incurring neurologic events such as a traumatic brain injury (TBI) or Cerebrovascular accident (CVA) can result in visual field loss. The field loss will often be projected to the same field of view for each eye. This means that a neurological event affecting the right cerebral cortex will cause a field loss in the left field of both eyes. This is termed a left homonymous hemianopsia. A lesion affecting the left cerebral cortex will produce a field loss for each eye on the right side. This is termed a right homonymous hemianopsia.

This type of vision impairment will cause significant interference in function and performance. Homonymous hemianopsias will directly affect spatial orientation, posture and balance. Persons with this resultant condition will frequently bump into objects on one side and are more Susceptible to injury from trauma or falls. This is due to the homonymous hemianopsia causing a Visual Midline Shift Syndrome (VMSS) which affects the concept of the ego center or visual midline in addition to the blind spot produced by the field loss. Also, it causes reading to become very difficult because right homonymous hemianopsia causes a spatial visual field loss which blocks the next word to be read. Consequently, a left homonymous hemianopsia causes difficulty in shifting gaze from the end of the line of print on the right side to the beginning of the next line of print.

In addition, homonymous hemianopsia interferes with daily living skills. Activities such as shopping in a store, conversing in a group of people, and even finding food on the plate will become very challenging. In turn, homonymous hemianopsia will affect socialization and reduce independence. A person with a homonymous hemianopsia is most often not safe to drive. This will in turn affect employment, earning potential, family relationships, to name several.

Homonymous hemianopsia can be determined behaviorally as well as clinically. Behaviorally, a person with a homonymous hemianopsia will have spatial difficulties causing bumping into objects, drifting when walking and/or not seeing objects on the side of the field loss. Clinically doctors will perform a visual field test to diagnose the condition. There are many different types of manual as well as automated visual field tests that require a response from the patient. All tests utilize a monocular assessment and require that the patient hold his or her fixation steady on a target. The standard automated instrument then projects sequential isolated lights that are timed to be presented in the peripheral field of the patient. The patient then presses a button each time he/she sees the light. The instrument then maps the visual field and corresponding field loss for each eye. When there is dysfunction of the ambient visual process, the focal system fails to discern the stimulus (for example, lights presented in the involved visual field).

Research has shown that the visual system is composed of at least two processes: focal and ambient. The focal visual process is primarily a function of the occipital cortex and orients to details related to higher cognitive process for attention. The ambient visual process is ambient and spatial in nature and is concerned with "where" objects are located relative to the observer and where the observer is located in space. The ambient visual process is continually anticipating change and acts as a balance against isolation or over-focalization on detail. It is here that information about a potential context (vertical and horizontal lines and boundaries in the peripheral field as well as orientation of the plane of the floor) is matched with sensory-motor information from the kinesthetic, proprioceptive and vestibular systems for organization of balance, posture, and movements. The ambient visual process organizes this information much faster than the focal process.

Following a neurological event such as a TBI, CVA, etc. dysfunction can occur interfering with the ambient spatial visual process. This leaves the focal visual process to isolate on detail without the spatial context from the ambient system. In turn, the affected focal visual process attempts to function, but it lacks the ability to adapt to changes and becomes bound on details.

It is the ambient visual process that releases the focal process from isolation. Also, the ambient visual process is continually anticipating change and acts as a balance against isolation or over-focalization on detail. Dysfunction between these processes causes slow reaction time and an inability to adapt to environmental changes. This condition has been called Post Trauma Vascular Syndrome (PTVS).

However, the present mode of visual field testing may be ineffective and inaccurate for assessment of dysfunction between the ambient and focal visual process. In turn, present automated field instruments may produce false negative results. Some persons actually report seeing the whole room, yet the automated instruments (perimeters) show a homonymous hemianopsia.

SUMMARY OF THE INVENTION

Additional features, functions and benefits of the disclosed systems and methods will be apparent from the detailed description which follows, particularly when read in conjunction with the accompanying figures.

In one embodiment, a method for creating a temporal-spatial dissociation between an ambient visual process and a focal visual process of a user is provided. The method includes rendering, via a parallactic ambient visual-field enhancing (PAVE) module configured to execute on a computing device communicatively coupled to a head mounted display device worn by a user, a fixation target and a background located behind the fixation target displayed within the head mounted display device. The method also includes updating, via the PAVE module, the rendering of the background within the head mounted display device, wherein the update comprises a virtual movement of the background behind the fixation target.

In another embodiment, a system for creating a temporal-spatial dissociation between an ambient visual process and a focal visual process of a user is provided. The system includes a head mounted holographic display device, a computing device communicatively coupled to the head mounted holographic display device worn by a user, and a parallactic ambient visual-field enhancing (PAVE) module configured to execute on the computing device. The diagnostic module when executed renders a fixation target and a background located behind the fixation target displayed within the head mounted display device. The diagnostic module when executed also updates the rendering of the background within the head mounted display device, wherein the update comprises a virtual movement of the background behind the fixation target.

In one embodiment, a non-transitory computer readable medium storing instructions executable by at least one processing device is provided. Execution of the instructions causes the at least one processing device to create a temporal-spatial dissociation between an ambient visual process and a focal visual process of a user, including rendering, via a parallactic ambient visual-field enhancing (PAVE) module configured to execute on a computing device communicatively coupled to a head mounted display device worn by a user, a fixation target and a background located behind the fixation target displayed within the head mounted display device, and updating, via the PAVE module, the rendering of the background within the head mounted display device, wherein the update comprises a virtual movement of the background behind the fixation target.

BRIEF DESCRIPTION OF DRAWINGS

Illustrative embodiments are shown by way of example in the accompanying drawings and should not be considered as a limitation of the present disclosure.

DETAILED DESCRIPTION

Figure 1:
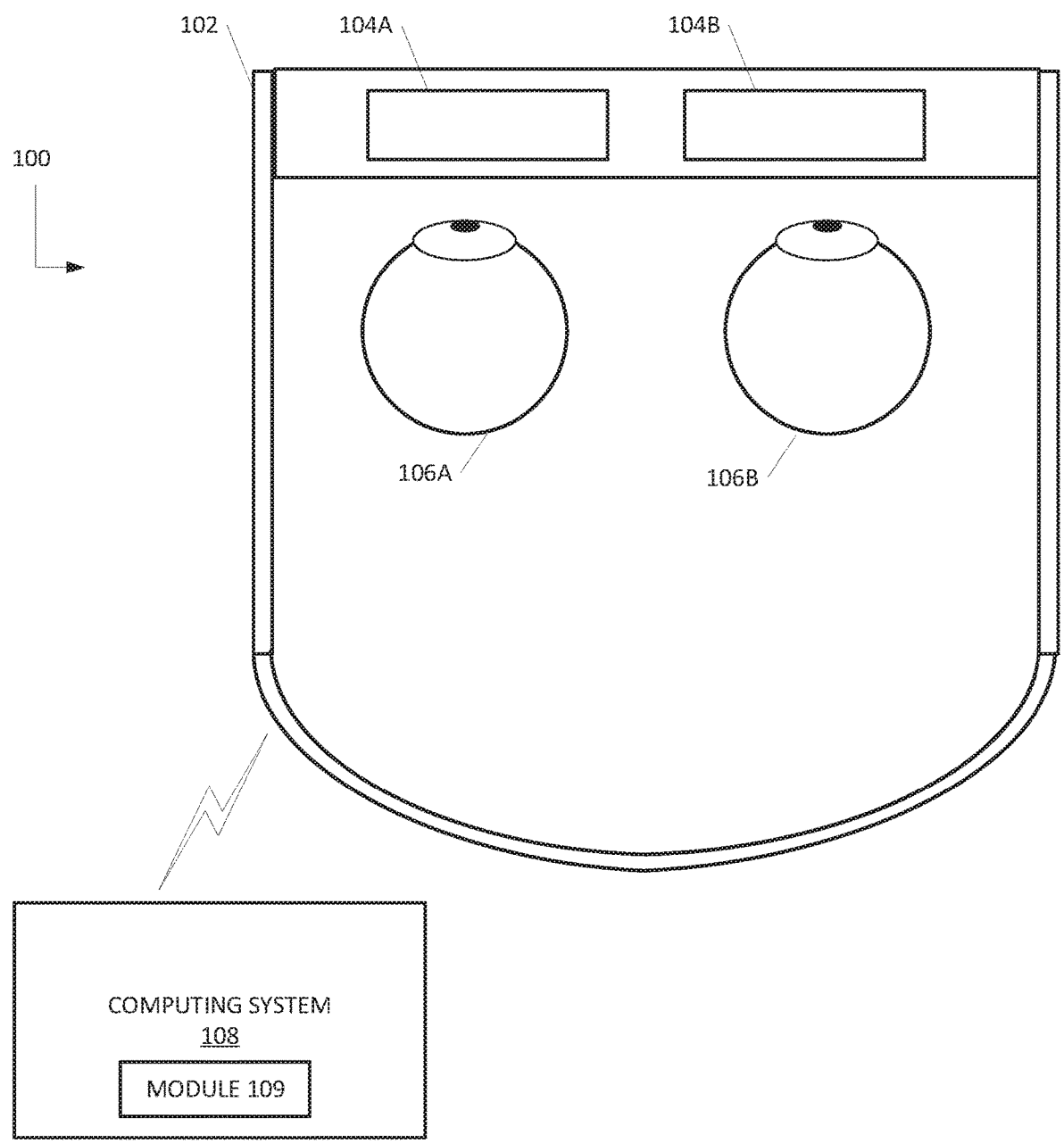
FIG. 1 is a block diagram illustrating a system for the parallactic ambient visual-field enhancing (PAVE) device according to an exemplary embodiment.

Systems, methods, a non-transitory computer readable medium, and an apparatus are described for a holographic and/or virtual parallactic ambient visual-field enhancer to create a temporal-spatial dissociation between the ambient and focal visual process. Example embodiments provide a parallactic ambient visual-field enhancing (PAVE) device for utilizing virtual reality and/or augmentative holographic projections to create the temporal-spatial dissociation. In an exemplary embodiment, the PAVE device is a head mounted holographic or virtual display device that renders a virtual and/or an augmented fixation target and a virtual and/or an augmented background separate from and behind the fixation target within a user's field of view.

The fixation target is a stationary virtual target for a user wearing the head-mounted PAVE device to focus on. The fixation target is separate from and located in front of the background. The fixation target may be rendered as, for example but not limited to, a shape (for example, a solid black circle, a circular outline, a diamond, or a prism) or an object (for example, a virtual or augmented person or vehicle). In some embodiments, the fixation target includes a pattern within an outline, for example, a circular outline that includes stripes within the circular outline in a same or different orientation from the background. The fixation target may be rendered in any location within the user's field of view and be large enough such that the user is able to focus or fixate on the target. In some embodiments, a clinician or administer may select and/or set the appearance and location of the fixation target.

In the exemplary embodiment, the background is a pattern of horizontal, diagonal, or vertical stripes, although other embodiments may include, but are not limited to, angled stripes, square waves, or sine waves. The pattern of stripes is projected to a distance either virtually or in the augmented field. The pattern of stripes may include colored and/or contrasting black and white stripes. The amplitude of the stripes can be changed to affect the width of the stripes. For example, contrast sensitivity can be adjusted to reduce a width of the stripes from low spatial frequency (wide stripes) to high spatial frequency (narrow stripes) or to increase the width of the stripes from high spatial frequency (narrow stripes) to low spatial frequency (wide stripes). Opacification can also be adjusted enabling transparency or dense opacification. In some embodiments, the clinician or administer may select and/or set the appearance of the background.

The PAVE device updates the rendering of the pattern. The update includes a virtual movement of the pattern either from left to right (horizontal), right to left (horizontal), up to down (vertical), down to up (vertical), or diagonal where is pattern is continually repeated during the movement. The frequency can be adjusted to affect a temporal speed of the movement. In some embodiments, the clinician or administer may select and/or set the movement of the background.

In the exemplary embodiment, the fixation target is presented to one eye while the background moves past the fixation target. In one embodiment, the parallactic field stimulation of the pattern (for example, stripes) will be presented for greatest effect to the eye with nasal field loss and the fixation target will be presented to the eye with temporal field loss. The stripes will move from the non-affected temporal field toward and into the eye with the affected nasal field loss. For a user with a field loss on the left side the stripes will move from right to left. As the user focalizes on the fixation target the user will begin to see the pattern moving in the affected field. While the user simultaneously views the moving background and the stationary fixation target the ambient and focal visual information of the user are disassociated and differentiated by the user simultaneously viewing the stationary fixation target and the moving background.

The pattern can be presented monocularly or binocularly and simulate parallax or relative movement around the fixation target. This condition has been effective by having the user fixate at a more distant or more near fixation target than where the pattern is projected, whereby the PAVE device creates a virtual or augmented environment incorporating parallax. It has been found that this disassociates the bi-modal visual process. It has been determined for those with a visual field loss have a compressed spatial or ambient visual field due to the neurological event. By disassociating the bi-modal visual process, it has been found the movement in a different plane enable a stable fixation point and the stripes simulate the parallactic experience. The result is that the spatial visual process begins to function thereby opening up the affected visual field.

In some embodiments, a visual indicator, such as but not limited to a cursor, star, or bull's eye, is further rendered in front of the background. The user can control the visual indicator, for example, using a joy stick or virtually using a hand or a touch controller. At a beginning of a session (a first time), the user is instructed to keep their eye fixated on the fixation target and move the visual indicator laterally to the maximum extent of continuing to see the visual indicator in the affected field. In other words, the user moves the visual indicator to the full extent laterally into the affected field while still being able to continue to fixate on the fixation target. Once the user moves the visual indicator to the full extent laterally into the affected field while continuing to see the fixation target, the PAVE device measures degrees of the visual indicator from the fixation target (a first degrees). At an end of the session (a second time), the user is instructed to repeat fixating on the fixation target and moving the visual indicator to an maximum extent of continuing to see the visual indicator in the affected field. Once the user moves the visual indicator to a full extent laterally into the affected field while continuing to see the fixation target, the degree field of the visual indicator from the fixation target is again measured (a second degrees). The difference between the degrees taken at the beginning (the first degrees at the first time) and the degrees taken at the end of the session (the second degrees at the second time) provides a difference or delta demonstrating change and improvement of the visual field. Thus, this embodiment provides a means of computing the delta between the initial degrees of field in the affected field from the fixation target and the enhanced or expanded degrees after a therapy session.

With repetition, the fixation target in combination with the activity causes the ambient visual process to differentiate separate from the focalization and user will report seeing the room and/or background (e.g., pattern) or more of the room and/or background on the other side of the fixation target. At first, the room and/or background may appear compressed and the movement of the room and/or background may appear to move faster on the affected side than the non-affected side. For example, the user may report seeing the room and/or background and movement only on the side related to the open visual field. The room and/or background appears to begin at the fixation target and is only seen on one side of the fixation target. With repetition, the field and movement will expand and slow down to match the field on the non-affected side enabling the user to see more of the room and/or background or the entire room and/or background in the scope of the field projected from their eyes. Over time, the field for many users will open because the ambient visual process becomes functional as a spatial system supporting focalization.

In some embodiments, for users with a peripheral compression of the visual field, a circular stripe pattern is utilized. The stripes can be animated to move from in to out or out to in. This movement has been found effective in a similar manner as previously described but instead of affecting only one side of the visual field, this rending opens the compression of the visual field in 360 degrees.

In some embodiments, the virtual fixation target and the virtual background are rendered in a virtualized environment that includes at least one of a virtual floor, a virtual ceiling, and/or one or more virtual walls. For example, the user may appear in a virtual room where the background (for example, the pattern of stripes) appears as a wall and the fixation target is located in front of the background. The virtual room may provide for a stabilization of the field. In other embodiments, the user may view the background within some or all of the user's field of view in the head-mounted PAVE device.

In some embodiments, the user wearing the head-mounted PAVE device walks around the stationary fixation target within a virtual or an augmented environment, such as the virtual room. In such an embodiment, the fixation target is rendered in the middle or center of the virtual room. Within the virtual or augmented environment, the pattern is rendered in the background. The user walks in a circle or circumference around the fixation target within the virtual environment. As the user walks around the fixation target, the focalization on the fixation target in the center of the circle that is walked appears stationary, but the virtual room will appear the rotate or spin in the background behind the fixation target opposite the direction that the user is walking.

In some embodiments, the background described above can be overlaid across a user's visual field with at least one virtual and/or augmented animation causing distraction to fixation and identification of important details. This will provide a means to enhance the quality of fixation and peripheral field awareness. This is especially useful for athletes, sharpshooters, pilots, or others who need to enhance their visual performance, particularly during environmental conditions that are distracting and interfering. For example, a quarterback must be able to scan the visual field for his/her receivers while maintaining awareness of his/her offensive line as well as the defense that is attempting to penetrate the 'pocket.' Often the distraction of the defensive players will cause the quarterback to miss an open receiver. A sharpshooter may have only a moment to identify a target and there often will be distractions. This is similar for the pilot, automobile or truck driver, and many others who have to maximize their vision to perform under environmental conditions that interfere or distract them from visual concentration. These users are also benefited by these activities because these activities train the bi-modal process how to maintain a balance by organizing focalization for fixation while maintaining the ambient visual process for fast and efficient release of fixation to the next intended spatially mapped point of fixation. The presented pattern distracts the user (for example, a quarterback) from fixation. The user will learn how to organize his/her vision and improve fixation through the animated field.

The described systems, methods, and apparatus have also been found to be effective for treating persons with vertigo, dizziness, and spatial dysfunction causing difficulty with mobility, ambulation and driving an automobile.

Some further advantages of the described systems, methods, and apparatus is that they are mobile, cost effective, automated, multi-lingual, and cloud based enabling the PAVE device to be controlled by a clinician, technician or therapist, and it can be provided as a home based therapy instrument that can be controlled remotely. In addition, it can serve a broader population of individuals since it is head mounted. The latter is important in order to serve persons with physical disabilities who may have a visual field loss. As a visual enhancement instrument, the virtual reality or augmentative reality PAVE device serves the purpose of enabling movement, particularly for the augmentative reality PAVE device that enables a user to see projected or augmented images in their own spatial visual field.

FIG. 1 is a block diagram illustrating a system 100 for the parallactic ambient visual-field enhancing (PAVE) device 100 according to an exemplary embodiment. In one embodiment, the PAVE device 100 can include a head mounted display (HMD) 102. The HMD 102 can include a pair of combiner lenses 104A, 104B for rendering a fixation target and a background within a user's field of view (FOV). The combiner lenses 104A, 104B can be calibrated to the inter-pupillary distance from the user's eyes 106A, 106B. A computing system 108 executing a parallactic ambient visual-field enhancing (PAVE) module 109 can be connected to the combiner lenses 104A, 104B. The PAVE device 100 can be repositioned in any of the nine primary gaze positions as needed. The PAVE device 100 is built to run on technical platforms that can project 2D and/or 3D holographic images and/or a virtual reality environment within a field of view provided by a wired or wireless headset. The HMD 102 can be connected to an adjustable, cushioned inner headband, which can tilt the combiner lenses 104A, 104B up and down, as well as forward and backward. To wear the unit, the user fits the HMD 102 on their head, using an adjustment wheel at the back of the headband to secure it around the crown, supporting and distributing the weight of the unit equally for comfort, before tilting the visor and combiner lenses 104A, 104B towards the front of the eyes.

The computing system 108 can be inclusive to the HMD 102, where the PAVE device 100 is a self-contained apparatus. The computing system 108 in the self contained apparatus can include additional power circuitry to provide electrical current to the parts of the computing system 108. Alternatively, the computing system 108 can be external to the HMD 102 and communicatively coupled either through wired or wireless communication channels to the HMD 102. Wired communication channels can include digital video transmission formats including High Definition Multimedia Interface (HDMI), DisplayPort™ (DisplayPort is a trademark of VESA of San Jose Calif., U.S.A.), or any other transmission format capable of propagating a video signal from the computing system 108 to the combiner lenses 104A, 104B. Additionally, the HMD 102 can include speakers or headphones for the presentation of instructional audio to the user during the disassociation. In a wireless communication embodiment, the HMD 102 can include a wireless adapter capable of low latency high bandwidth applications, including but not limited to IEEE 802.11ad. The wireless adapter can interface with the computing system 108 for the transmission of low latency video to be displayed upon the combiner lenses 104, 104B.

Additionally the computing system 108 can include software for the manipulation and rendering of 2D and/or 3D virtual targets and backgrounds within a virtual space. The software can include both platform software to support any fundamental functionality of the HMD 102, such as motion tracking, input functionality, and eye tracking. Platform software can be implemented in a virtual reality (VR) framework, augmented reality (AR) framework, or mixed reality (MR) framework. Platform software to support the fundamental functionality can include but are not limited to SteamVR® (SteamVR is a registered trademark of the Valve Corporation, Seattle Wash., U.S.A) software development kit (SDK), Oculus® VR SDK (Oculus is a registered trademark of Oculus VR LLC, Irvine Calif., U.S.A.), OSVR (Open source VR) (OSVR is a registered trademark of Razer Asia Pacific Pte. Ltd. Singapore) SDK, and Microsoft Windows Mixed Reality Computing Platform. Application software executing on the computing system 108 with the underlying platform software can be a customized rendering engine, or an off-the-shelf 2D and/or 3D rendering framework, such as Unity® Software (Unity Software is a registered trademark of Unity Technologies of San Francisco Calif., U.S.A). The rendering framework can provide the basic building blocks of the virtualized environment, including 3D objects and manipulation techniques to render movement and/or change the appearance of the 2D and/or 3D targets and backgrounds. The rendering framework can provide application programming interfaces (APIs) for the instantiation of 2D and/or 3D virtual patterns and well-defined interfaces for the manipulation of the 2D and/or 3D targets and backgrounds within the framework. Common software programming language bindings for rendering frameworks include but are not limited to C++, Java, and C#. Additionally, the application software can provide settings to allow a test administrator to adjust actions within the test, such as background type (e.g., stripes, waves, etc.), background movement direction, background movement speed, pattern orientation, and fixation target type (e.g., solid dot, pattern, etc.).

Figure 2:
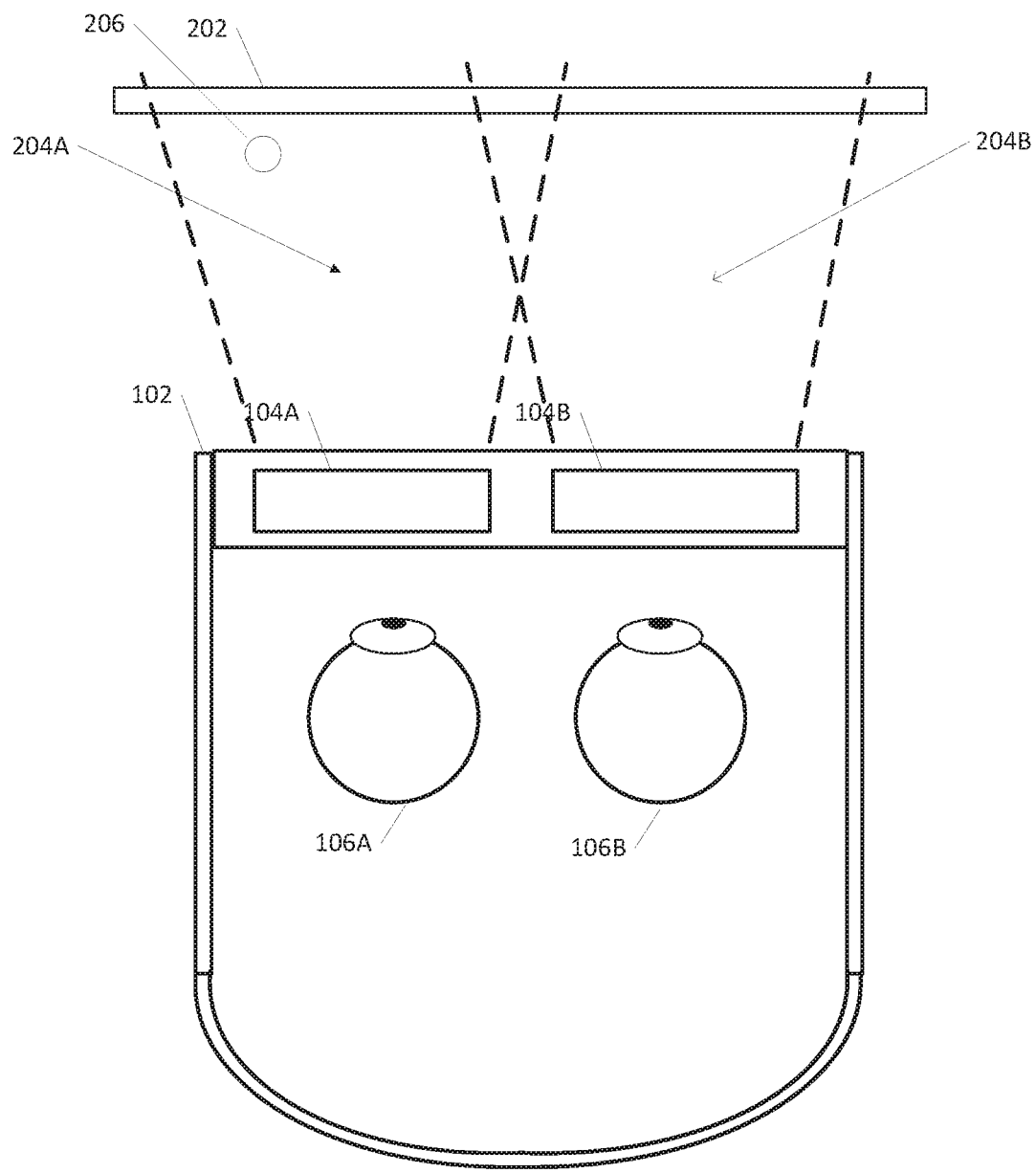
FIGS. 2 and 3 are diagrams illustrating a fixation target and background to create a temporal-spatial dissociation between the ambient and focal visual process using the PAVE device according to an exemplary embodiment.
Figure 3:
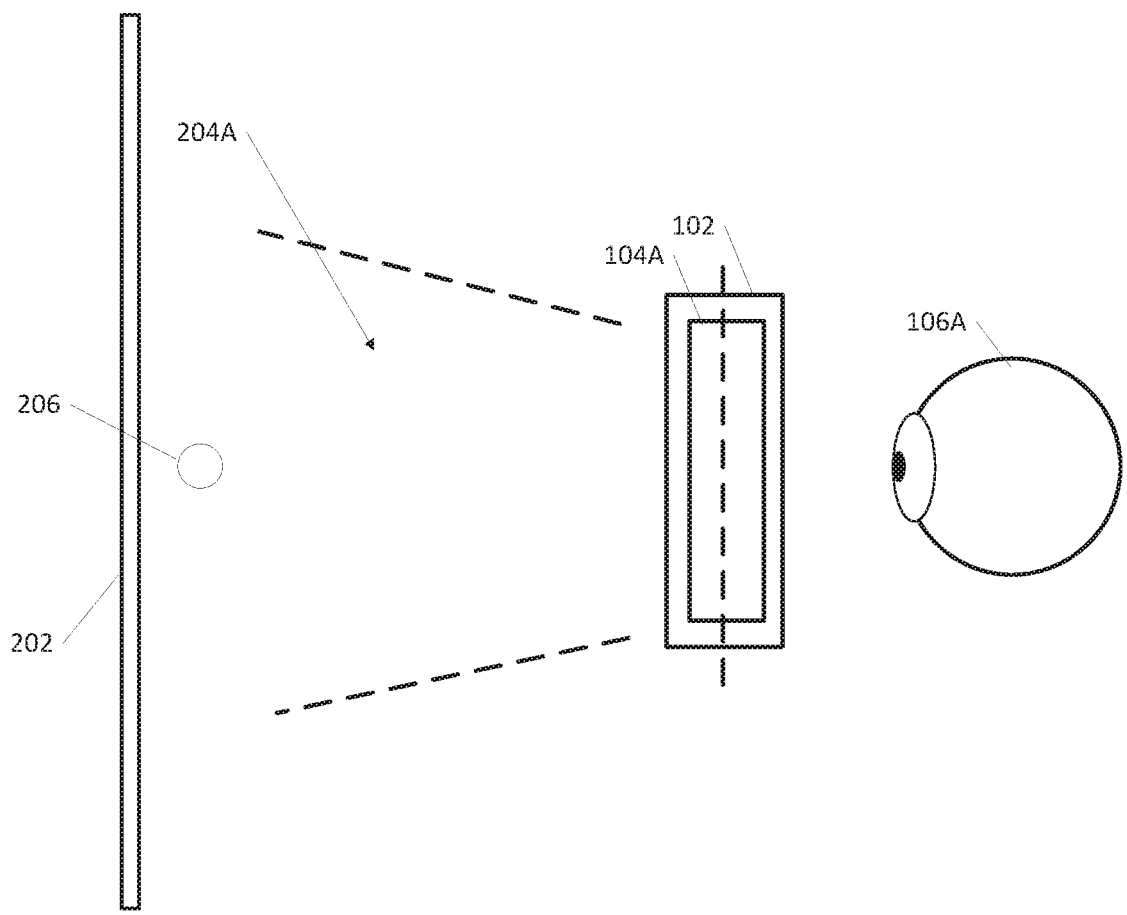

FIGS. 2 and 3 are diagrams illustrating a fixation target and background to create a temporal-spatial dissociation between the ambient and focal visual process using a parallactic ambient visual-field enhancing (PAVE) device according to an exemplary embodiment. In one embodiment, a fixation target 206 is rendered stationary in a user's field of view (FOV) 204A and/or 204B while a background 202 is rendered behind the fixation target 206 and manipulated within the user's field of view (FOV) 204A, 204B. Utilizing application software, the background 202 is translated and projected on the combiner lenses 104A, 104B to give the appearance that the background 202 is a set distance from the view of the user's eyes 106A, 106B. Similarly, the fixation target 206 is translated and projected on the combiner lenses 104A and/or 104B to give the appearance that the fixation target 206 is a set distance from the view of the user's eyes 106A and/or 106B. For example, in some embodiments, the presentation of the background 202 and/or the fixation target 206 can correspond to projection of the background 202 and/or the fixation target 206 at distances of 16 inches to 20 feet in front of the user's eyes 106A, 106B. The fixation target 206 may be closer to or further from the background 202 than shown in the figures.

The background 202 is rendered moving left to right, right to left, up to down, or down to up in the user's FOV 204A, 204B. A fixation target 206 is presented to one eye while the background 202 move past the fixation target 206. For a user with a field loss on the left side the background 202 will move from right to left. As the user focalizes on the fixation target 206 the user will begin to see the background 202 moving in the affected field.

In some embodiments, the user can provide input to the application software or platform software. The input can take the form of voice commands, gestures, or input from a "clicker." For example, the user can provide input to begin or stop motion of the background 202. In one embodiment, the user can start the test by providing input to the computing system 108. The input can take the form of voice commands, including saying key words indicative of beginning the test, gestures or providing input from a "clicker." The user states the word "start" to begin the movement of the background 202. In some embodiment, the user can provide input to stop the movement of the background 202 in the form of a voice command of "stop." In some embodiments, the width, color, or other aspects of the background 202 can be controlled via voice commands including "change color," "change direction," "increase width," and "decrease width."

Figure 4:
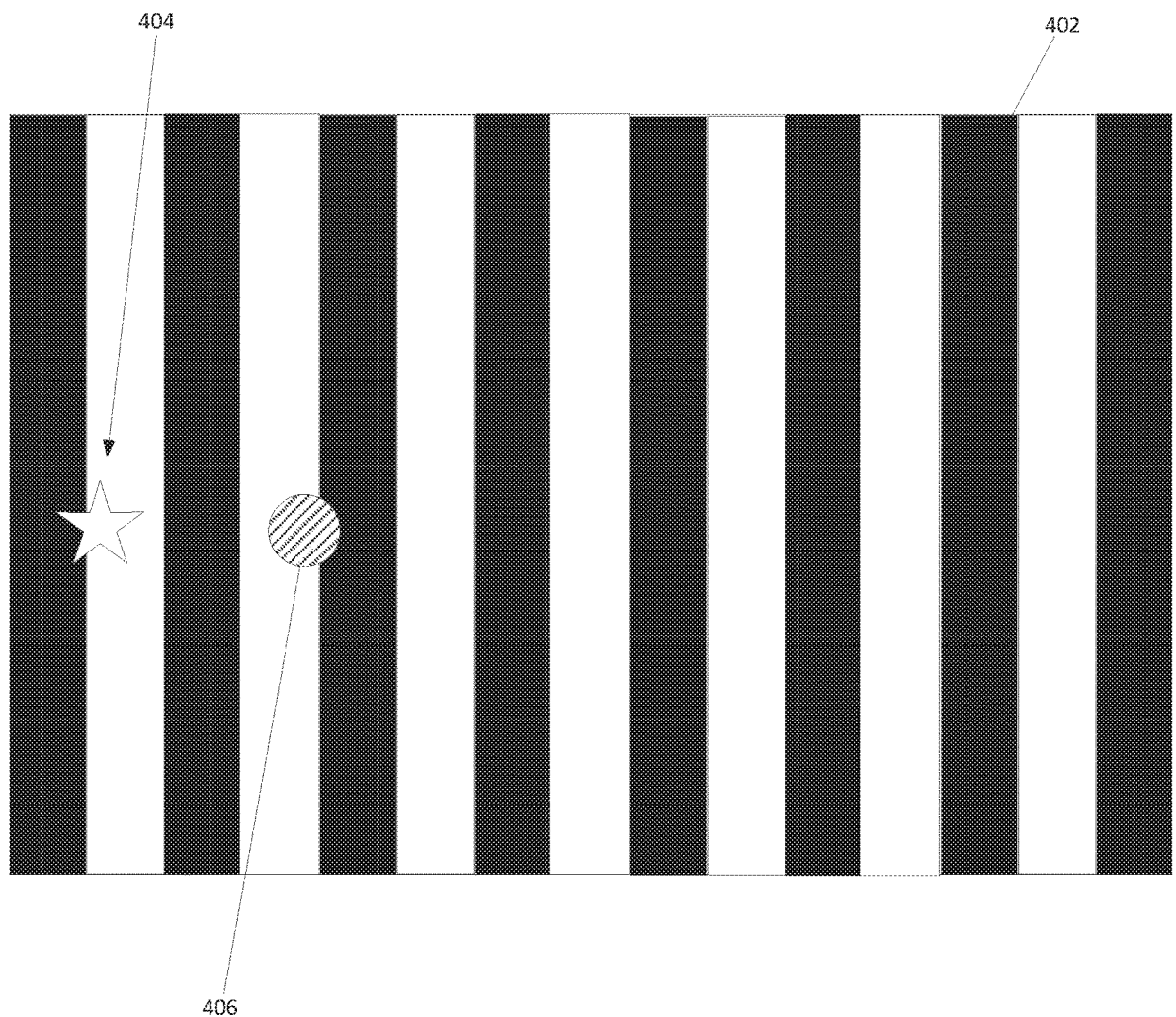
FIG. 4 illustrates an exemplary background and fixation target in accordance with an exemplary embodiment.

FIG. 4 illustrates an exemplary background 402 and fixation target 406 as described herein and in accordance with an exemplary embodiment. In the exemplary embodiment, the background 402 includes a pattern of contrasting black and white stripes. The background 202 can be manipulated in a user's field of view. In the exemplary embodiment, the fixation target 406 is a stationary circle that includes black and white stripes of a different orientation from the background 402. The fixation target 406 is located in front of the background 402. However, in other embodiments, the background 402 may include a different pattern and/or stripes of a different orientation, color, and/or width, and the fixation target 406 may include a different style (e.g., solid, dotted, etc.), color, pattern, size, and/or location within the background 402.

In some embodiments, a visual indicator 404 (shown as a star) is rendered in front of the background 402 along with the fixation target 406. The user can control the visual indicator 404, for example, using a joy stick or virtually using a hand or a touch controller. At a beginning of a session, the user is instructed to keep their eye fixated on the fixation target 406 and move the visual indicator 404 laterally to the maximum extent of continuing to see the visual indicator 404 in the affected field. The PAVE device measures degrees of the visual indicator 404 from the fixation target 406. At an end of the session, the user is instructed to repeat fixating on the fixation target 406 and again move the visual indicator 404 to the maximum extent seen into the affected field. The PAVE device again measures the degrees field, which provides a difference or delta demonstrating change and/or an improvement of the visual field.

Figure 5:
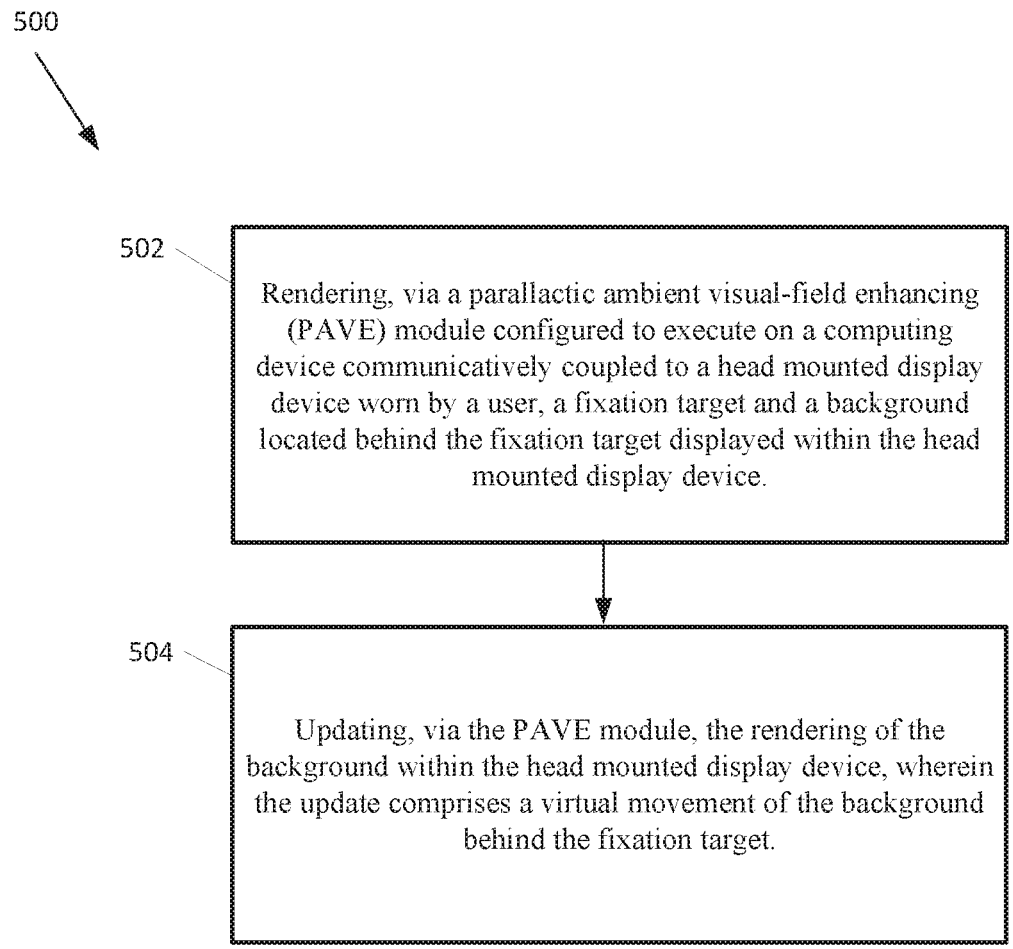
FIG. 5 illustrates a method for providing a parallactic ambient visual-field enhancer to create a temporal-spatial dissociation between an ambient and focal visual process of a user in accordance with an exemplary embodiment.

FIG. 5 illustrates a method 500 for providing a parallactic ambient visual-field enhancer to create a temporal-spatial dissociation between an ambient and focal visual process of a user in accordance with an exemplary embodiment.

At step 502, a parallactic ambient visual-field enhancing (PAVE) module configured to execute on a computing device communicatively coupled to a head mounted display device worn by a user renders a fixation target and a background located behind the fixation target displayed within the head mounted display device.

At step 504, the PAVE module updates the rendering of the background within the head mounted display device, wherein the update comprises a virtual movement of the background behind the fixation target.

Figure 6:
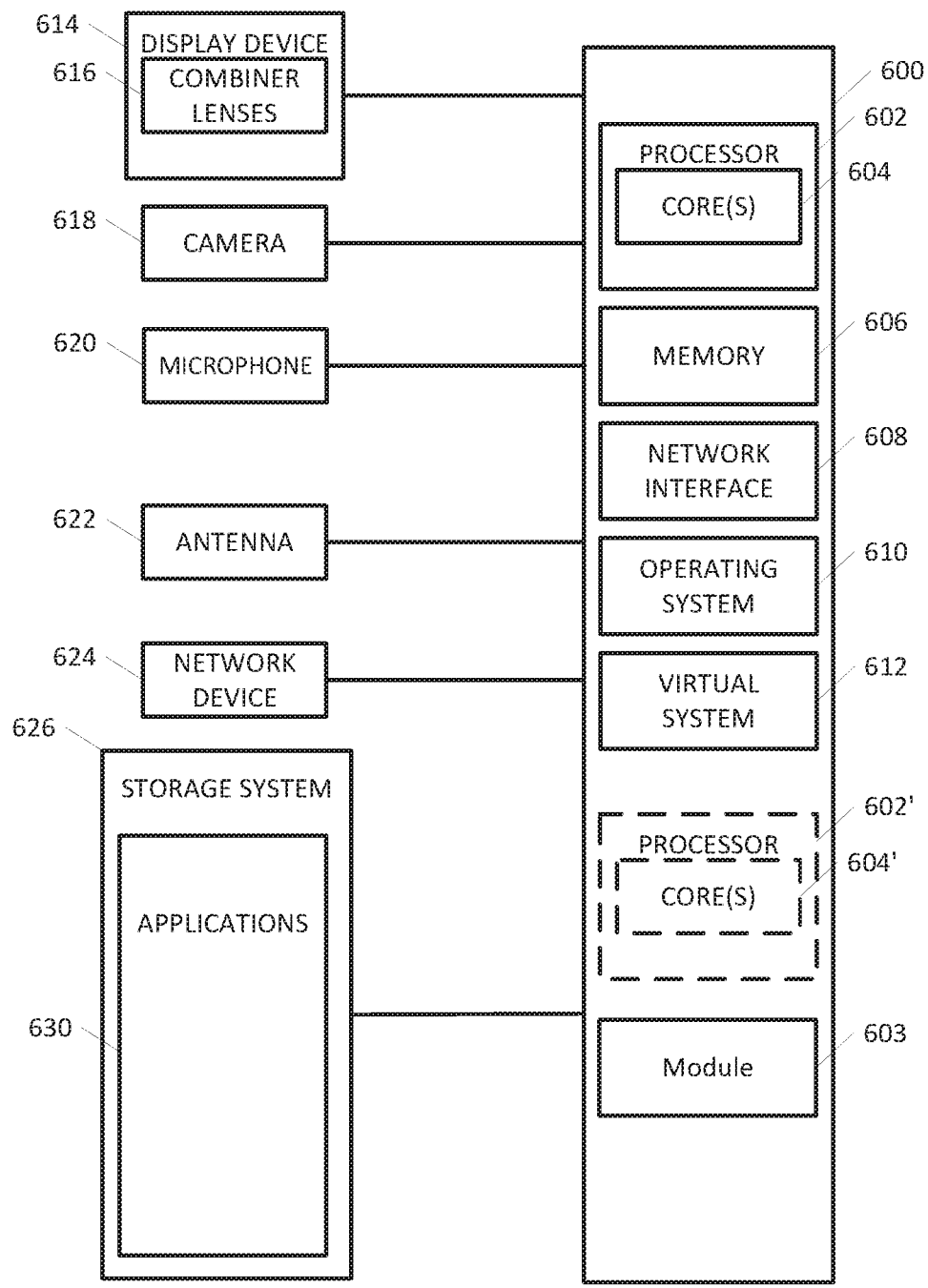
FIG. 6 depicts a block diagram an exemplary computing device in accordance with an exemplary embodiment.

FIG. 6 depicts a block diagram an exemplary computing device 600 in accordance with an exemplary embodiment. Computing device 600 may include computing device 108 for implementing the parallactic ambient visual-field enhancer. For example, the computing device 600 can be embodied as a portion of the parallactic ambient visual-field enhancing (PAVE) device worn by a user and/or communicatively coupled to the PAVE device worn by the user, and supporting computing devices. A parallactic ambient visual-field enhancing (PAVE) module 603 is configured to execute on the computing device 600 to render and update the background and fixation target within the PAVE device, as described herein.

The computing device 600 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives, one or more solid state disks), and the like. For example, memory 606 included in the computing system 600 may store computer-readable and computer-executable instructions or software (e.g., applications 630 such as rendering application) for implementing exemplary operations of the computing device 600. The computing system 600 also includes configurable and/or programmable processor 602 and associated core(s) 604, and optionally, one or more additional configurable and/or programmable processor(s) 602' and associated core(s) 604' (for example, in the case of computer systems having multiple processors/cores), for executing computer-readable and computer-executable instructions or software stored in the memory 606 and other programs for implementing exemplary embodiments of the present disclosure. Processor 602 and processor(s) 602' may each be a single core processor or multiple core (604 and 604') processor. Either or both of processor 602 and processor(s) 602' may be configured to execute one or more of the instructions described in connection with computing system 600.

Virtualization may be employed in the computing system 600 so that infrastructure and resources in the computing system 600 may be shared dynamically. A virtual machine 612 may be provided to handle a process running on multiple processors so that the process appears to be using only one computing resource rather than multiple computing resources. Multiple virtual machines may also be used with one processor.

Memory 606 may include a computer system memory or random access memory, such as DRAM, SRAM, EDO RAM, and the like. Memory 606 may include other types of memory as well, or combinations thereof. The computing system 600 can receive data from input/output devices. A user may interact with the computing system 600 through a visual display device 614, such as a combiner lenses 616, which may display one or more virtual graphical user interfaces, a microphone 620 and one or more cameras 618.

The computing system 600 may also include one or more storage devices 626, such as a hard-drive, CD-ROM, or other computer readable media, for storing data and computer-readable instructions and/or software that implement exemplary embodiments of the present disclosure. For example, exemplary storage device 626 can include storing information associated with platform software and the application software.

The computing system 600 can include a network interface 608 configured to interface via one or more network devices 624 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing system can include one or more antennas 622 to facilitate wireless communication (e.g., via the network interface) between the computing system 600 and a network and/or between the computing system 600 and other computing devices. The network interface 608 may include a built-in network adapter, network interface card, PCMCIA network card, card bus network adapter, wireless network adapter, USB network adapter, modem or any other device suitable for interfacing the computing system 600 to any type of network capable of communication and performing the operations described herein.

The computing system 600 may run any operating system 610, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing system 600 and performing the operations described herein. In exemplary embodiments, the operating system 610 may be run in native mode or emulated mode. In an exemplary embodiment, the operating system 610 may be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes multiple system elements, device components, or method steps, those elements, components, or steps can be replaced with a single element, component, or step. Likewise, a single element, component, or step can be replaced with multiple elements, components, or steps that serve the same purpose. Moreover, while exemplary embodiments have been shown and described with references to particular embodiments thereof, those of ordinary skill in the art will understand that various substitutions and alterations in form and detail can be made therein without departing from the scope of the present disclosure. Further, still, other aspects, functions, and advantages are also within the scope of the present disclosure.

Exemplary flowcharts are provided herein for illustrative purposes and are non-limiting examples of methods. One of ordinary skill in the art will recognize that exemplary methods can include more or fewer steps than those illustrated in the exemplary flowcharts and that the steps in the exemplary flowcharts can be performed in a different order than the order shown in the illustrative flowcharts.

We claim:

1. A method for creating a temporal-spatial dissociation between an ambient visual process and a focal visual process of a user, comprising:
    rendering, via a parallactic ambient visual-field enhancing (PAVE) module configured to execute on a computing device communicatively coupled to a head mounted display device worn by a user, a fixation target and a background located behind the fixation target displayed within the head mounted display device; and
    updating, via the PAVE module, the rendering of the background within the head mounted display device, wherein the update comprises a virtual movement of the background behind the fixation target;
    whereby ambient visual information and focal visual information of the user are dissociated.

2. The method of claim 1, wherein the background comprises a pattern of stripes or waves.

3. The method of claim 1, wherein the virtual movement comprises a vertical, diagonal, or horizontal movement.

4. The method of claim 1, wherein the fixation target is stationary.

5. The method of claim 1, wherein the fixation target comprises a shape or an object.

6. The method of claim 1, wherein the fixation target and the background are generated in virtual reality or augmented reality.

7. The method of claim 1, further comprising:
    rendering, via the PAVE module, a virtual indicator displayed within the head mounted display device;
    receiving, via the PAVE module, a lateral movement of the virtual indicator at a first time;
    measuring, via the PAVE module at the first time, a first degrees of the visual indicator from the fixation target;
    receiving, via the PAVE module, a lateral movement of the virtual indicator at a second time;
    measuring, via the PAVE module at the second time, a second degrees of the visual indicator from the fixation target; and
    computing, via the PAVE module, a delta between the first degrees and the second degrees.

8. A system for creating a temporal-spatial dissociation between an ambient visual process and a focal visual process of a user, comprising:
    a head mounted holographic display device;
    a computing device communicatively coupled to the head mounted holographic display device worn by a user;
    a parallactic ambient visual-field enhancing (PAVE) module configured to execute on the computing device, the PAVE module when executed:
        renders a fixation target and a background located behind the fixation target displayed within the head mounted display device; and
        updates the rendering of the background within the head mounted display device, wherein the update comprises a virtual movement of the background behind the fixation target, and whereby ambient visual information and focal visual information of the user are dissociated.

9. The system of claim 8, wherein the background comprises a pattern of stripes or waves.

10. The system of claim 8, wherein the virtual movement comprises a vertical, diagonal, or horizontal movement.

11. The system of claim 8, wherein the fixation target is stationary.

12. The system of claim 8, wherein the fixation target comprises a shape or an object.

13. The system of claim 8, wherein the fixation target and the background are generated in virtual reality or augmented reality.

14. The system of claim 8, the PAVE module further configured to:
- render, via the PAVE module, a virtual indicator displayed within the head mounted display device;
- receive, via the PAVE module, a lateral movement of the virtual indicator at a first time;
- measure, via the PAVE module at the first time, a first degrees of the visual indicator from the fixation target;
- receive, via the PAVE module, a lateral movement of the virtual indicator at a second time;
- measuring, via the PAVE module at the second time, a second degrees of the visual indicator from the fixation target; and
- computing, via the PAVE module, a delta between the first degrees and the second degrees.

15. A non-transitory computer readable medium storing instructions executable by at least one processing device, wherein execution of the instructions causes the at least one processing device to create a temporal-spatial dissociation between an ambient visual process and a focal visual process of a user, comprising:
- rendering, via a parallactic ambient visual-field enhancing (PAVE) module configured to execute on a computing device communicatively coupled to a head mounted display device worn by a user, a fixation target and a background located behind the fixation target displayed within the head mounted display device; and
- updating, via the PAVE module, the rendering of the background within the head mounted display device, wherein the update comprises a virtual movement of the background behind the fixation target, and whereby ambient visual information and focal visual information of the user are dissociated.

16. The non-transitory computer readable medium of claim 15, wherein the background comprises a pattern of stripes or waves.

17. The non-transitory computer readable medium of claim 15, wherein the virtual movement comprises a vertical, diagonal, or horizontal movement.

18. The non-transitory computer readable medium of claim 15, wherein the fixation target is stationary.

19. The non-transitory computer readable medium of claim 15, wherein the fixation target comprises a shape or an object.

20. The non-transitory computer readable medium of claim 15, wherein the fixation target and the background are generated in virtual reality or augmented reality.

* * * * *